(12) United States Patent
Van Dijk et al.

(10) Patent No.: US 10,736,588 B2
(45) Date of Patent: Aug. 11, 2020

(54) INTERVENTIONAL X-RAY

(71) Applicant: KONINKLIJKE PHILIPS N.V., Eindhoven (NL)

(72) Inventors: Erik Martinus Hubertus Petrus Van Dijk, Den Bosch (NL); Sander Slegt, Best (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 688 days.

(21) Appl. No.: 14/781,334

(22) PCT Filed: Apr. 2, 2014

(86) PCT No.: PCT/IB2014/060377
§ 371 (c)(1),
(2) Date: Sep. 30, 2015

(87) PCT Pub. No.: WO2014/162275
PCT Pub. Date: Oct. 9, 2014

(65) Prior Publication Data
US 2016/0029981 A1 Feb. 4, 2016

Related U.S. Application Data

(60) Provisional application No. 61/807,820, filed on Apr. 3, 2013.

(51) Int. Cl.
*A61B 6/12* (2006.01)
*A61B 6/06* (2006.01)
(Continued)

(52) U.S. Cl.
CPC .......... *A61B 6/12* (2013.01); *A61B 6/06* (2013.01); *A61B 6/467* (2013.01); *A61B 6/54* (2013.01);
(Continued)

(58) Field of Classification Search
None
See application file for complete search history.

(56) References Cited

U.S. PATENT DOCUMENTS 5,369,678 A * 11/1994 Chiu ................. A61B 6/06
378/152
5,730,129 A * 3/1998 Darrow ............. A61B 5/055
128/899
(Continued)

FOREIGN PATENT DOCUMENTS

JP 2006130158 A 5/2006
WO 2005009243 A1 2/2005
(Continued)

OTHER PUBLICATIONS

Yaniv et al., "Electromagnetic tracking in the clinical environment", Medical Physics, vol. 36, No. 3, Mar. 2009 (Year: 2009).*
(Continued)

*Primary Examiner* — Joanne M Hoffman

(57) ABSTRACT

An interventional system includes an introduction element (4) such as a catheter for being introduced into an object (9), for instance, a person. A moving unit (2) such as a robot moves the introduction element within the object. A tracking image generating unit (3) generates, using a radiation beam (7), tracking images of the introduction element within the object. A controller (8) controls the tracking image generating unit depending on movement parameters of the moving unit, which are indicative of the movement. The control operation of the controller (8) allows reducing radiation dose applied to the object.

13 Claims, 2 Drawing Sheets

(51) Int. Cl.
*A61B 6/00* (2006.01)
*A61B 34/30* (2016.01)
*A61B 34/20* (2016.01)
*A61B 90/00* (2016.01)

(52) U.S. Cl.
CPC .............. *A61B 6/542* (2013.01); *A61B 34/30* (2016.02); *A61B 6/4441* (2013.01); *A61B 2034/2059* (2016.02); *A61B 2034/2065* (2016.02); *A61B 2090/376* (2016.02)

(56) References Cited

U.S. PATENT DOCUMENTS

| | | | | |
|---|---|---|---|---|
| 6,493,575 | B1 * | 12/2002 | Kesten | A61B 90/36 600/431 |
| 6,785,572 | B2 * | 8/2004 | Yanof | A61B 34/70 600/411 |
| 7,822,241 | B2 * | 10/2010 | Eck | A61B 6/12 382/128 |
| 7,826,884 | B2 * | 11/2010 | Baumgart | A61B 6/463 378/62 |
| 8,265,224 | B2 * | 9/2012 | Baumgart | A61B 6/12 378/114 |
| 8,965,072 | B2 * | 2/2015 | Fujii | A61B 6/12 382/128 |
| 9,131,908 | B2 * | 9/2015 | Shimizu | A61B 6/022 |
| 9,445,772 | B2 * | 9/2016 | Callaghan | A61B 6/12 |
| 9,592,014 | B2 * | 3/2017 | Melman | A61B 6/06 |
| 9,724,061 | B2 * | 8/2017 | Hyung | A61B 6/469 |
| 9,936,933 | B2 * | 4/2018 | Lim | A61B 6/08 |
| 2004/0044279 | A1 | 3/2004 | Lewin | |
| 2005/0054910 | A1 * | 3/2005 | Tremblay | A61B 5/055 600/411 |
| 2006/0149147 | A1 * | 7/2006 | Yanof | A61B 6/12 600/424 |
| 2006/0241465 | A1 * | 10/2006 | Huennekens | A61B 6/504 600/458 |
| 2006/0247520 | A1 * | 11/2006 | McGee | A61B 6/12 600/434 |
| 2007/0197896 | A1 | 8/2007 | Moll et al. | |
| 2008/0319297 | A1 * | 12/2008 | Danehorn | A61M 25/01 600/373 |
| 2010/0061509 | A1 * | 3/2010 | D'Ambrosio | A61B 6/10 378/62 |
| 2010/0063514 | A1 * | 3/2010 | Maschke | A61B 5/1135 606/130 |
| 2010/0272238 | A1 * | 10/2010 | Machan | A61B 6/06 378/98.2 |
| 2010/0274120 | A1 * | 10/2010 | Heuscher | A61B 6/032 600/424 |
| 2011/0178532 | A1 * | 7/2011 | Amiri | A61M 25/0147 606/130 |
| 2012/0179167 | A1 * | 7/2012 | Wenderow | A61B 34/30 606/130 |
| 2014/0276684 | A1 * | 9/2014 | Huennekens | A61B 17/320758 606/7 |

FOREIGN PATENT DOCUMENTS

| | | |
|---|---|---|
| WO | 2006116748 A1 | 11/2006 |
| WO | 2012056386 A1 | 5/2012 |
| WO | 2012077011 A1 | 6/2012 |
| WO | 2012123850 A1 | 9/2012 |
| WO | 2012129374 A1 | 9/2012 |
| WO | 2014033573 A1 | 3/2014 |
| WO | 2014053970 A1 | 4/2014 |
| WO | 2014057393 A1 | 4/2014 |
| WO | 2014091390 A1 | 6/2014 |

OTHER PUBLICATIONS

Ostrovsky, Gene, "Philips Adding Corindus' Percutaneous Coronary Intervention Robotics to Its Cardiology Solutions"; www.medgadget.com/2011/04/philips_adding_corindus_percutaneous_coronary.

* cited by examiner

INTERVENTIONAL X-RAY

CROSS-REFERENCE TO PRIOR APPLICATIONS

This application is the U.S. National Phase application under 35 U.S.C. § 371 of International Application No. PCT/IB2014/060377, filed on Apr. 2, 2014, which claims the benefit of U.S. Provisional Patent Application No. 61/807,820, filed on Apr. 3, 2013. These applications are hereby incorporated by reference herein.

FIELD OF THE INVENTION

The invention relates to an interventional system, to an interventional method, to a computer program element, and to a computer readable medium.

BACKGROUND OF THE INVENTION

WO 2005/009243 A1 discloses an x-ray unit for generating images of a body, wherein the x-ray unit comprises an x-ray source, an automatically adjustable collimator for limiting, locally attenuating and/or filtering an x-ray beam, an x-ray detector and a data processing unit that is coupled to the collimator and the x-ray detector. The data processing unit is adapted to localize a region of interest inside the body on at least a first x-ray image of the body transmitted by the x-ray detector and to adjust the collimator such that subsequent x-ray images are concentrated on the region of interest.

It has been observed however, that operation of this or similar x-ray units at times still attract a relatively large radiation dose despite using the collimator for x-ray beam restriction.

SUMMARY OF THE INVENTION

There may therefore be a need for an apparatus to improve the radiation dosage balance. It should be noted that the following described aspect of the invention equally apply to the interventional method, to the computer program element and to the computer readable medium.

According to a first aspect of the invention there is provided an interventional system comprising:
   an introduction element for being introduced into an object
   a moving unit for moving the introduction element within the object,
   a tracking image generating unit (also referred to herein as "imager") for generating, using a radiation beam, a tracking image of the introduction element within the object, and
   a controller for controlling the tracking image generating unit,
wherein the moving unit is adapted to provide a movement parameter to the tracking image generating unit, wherein the movement parameter holds information about the movement of the introduction element within the object caused by the moving unit, and wherein the controller is configured to control operation of the tracking image generating unit in dependence on the provided movement parameter fulfilling a movement condition.

In one embodiment, the control operation concerns the radiation beam. More specifically, control operation concerns generation or modification of the imager's radiation beam. Yet more specifically, according to one embodiment, the controlling by the controller includes any one or a combination of i) switching on or off a radiation source of the tracking image generating unit capable of generating the radiation beam detectable by a detector of the tracking image generating unit after the beam's traversal of the object or ii) increasing or decreasing a frame rate of the tracking image generating unit, or iii) increasing or decreasing the beam's intensity or iv) increasing or decreasing an aperture of a collimator of the tracking image generating unit.

In short, the controller allows to (automatically) i) generate the x-ray beam when it is needed and allows modifying the beam so it can be used where it is needed. The movement parameters generated by the movement unit are harnessed for the control operation and the control operation is effected once the movement parameter fulfills the (user definable) movement condition. The control operation is in some embodiment automatic in the sense that no user-imager interaction is required although in some embodiments there are "override" functionalities envisaged so that the user can still control the imager.

More specifically, and according to one embodiment, the controller operates to switch on the radiation source if the provided movement parameter indicates i) that the introduction element moved at least a pre-defined distance and/or ii) that the speed of the introduction element is in excess of a pre-defined speed threshold. In this embodiment, the movement condition is expressed in terms of the pre-defined distance and/or pre-defined speed threshold. In some embodiments, the movement parameter records an orientation (left, right, forward, backward) of the movement. In other words, the movement parameter records "kinematic events" experienced by the introduction element as it is moved through the object. In one embodiment, the introduction element is a catheter and the object is a human or animal patient. Interventions where the proposed system can be put to use are PCI or similar interventions. In sum, the system affords to the user safe navigation of the catheter through the patient at a very low dosage cost because, for instance, the beam is used only in circumstances were detailed imagery is needed.

According to one embodiment, a user input device is configured to issue upon user interaction a request to change operation of the tracking image generating unit, wherein the controller blocks said request until the provided movement parameter indicates that the movement parameter fulfills the movement condition.

According to one embodiment, the controller is configured to cease, responsive to an override request, the blocking operation even though the movement parameter does not fulfill the movement condition.

In one exemplary embodiment, the controller blocks the request to switch on the x-ray source until the provided movement parameter indicates that the movement parameter fulfills the movement condition. This allows protecting the patient from radiation over dosage for instance when an inexperienced user operates the system.

According to one embodiment, the interventional system further comprises a position determination unit for determining a position of the introduction element within the object based on the movement parameter, wherein the controlling of the tracking image generating unit's operation is in dependence on the determined position of the introduction element.

More specifically, and according to one exemplary embodiment, controlling of the tracking image generating unit's operation includes switching on the radiation source or increasing the collimator aperture, wherein switching on the radiation source or the increasing of the collimator aperture occurs only if the determined position of the introduction element exceeds a distance threshold. This operation allows "cold tracking". In this embodiment it is envisaged that the user is supported by a roadmap imagery (as will be explained in more detail below) shown on a screen, with a suitable indicator updated on the screen according to the received movement parameter. No live exposures are acquired during the cold tracking. In other words the path outlined on the roadmap imagery is an estimate based solely on the received movement parameter. However, if the movement parameter fulfills the movement condition for example if the movement parameter indicates that the catheter has traveled beyond a certain distance threshold or at high speed, an exposure is triggered to acquire a new up-to-date live image. In other words the estimated roadmap path can be "reality checked".

According to one embodiment, the controller controls a frame rate of the radiation source. According to one embodiment, the frame rate is increased or decreased in dependence on the determined position of the introduction element. Specifically and according to an exemplary embodiment, the movement parameter records a speed and/or a distance traveled, wherein the frame rate is the higher the lower the speed or the lower the distance traveled.

According to one embodiment, the introduction element is introduced into the object through an ingress point and follows a path through the object, wherein the controlling of the tracking image generating unit's operation is in dependence on the position determination unit registering that the introduction element is moved in forward motion along said path in respect of said ingress point and/or wherein the controlling of the tracking image generating unit's operation is in dependence on the position determination unit registering that the introduction element is moved in backwards motion along said path in respect of said ingress point.

According to one exemplary embodiment, the frame rate is increased if the position determination unit registers that the introduction element is moved in forward motion along said path in respect of the said ingress point and/or wherein frame rate is decreased if the position determination unit registers that the introduction element is moved in backwards motion along said path in respect of the said ingress point.

According to one embodiment, the controlling of the tracking image generating unit's operation is in dependence on the position determination unit registering that the introduction element is within or outside a pre-defined distance of a target in the object.

According to one embodiment, the frame rate is increased or decreased upon the position determination unit registering that the introduction element is within or outside a pre-defined distance of the target in the object.

In the previous embodiments, instead of or in addition to changing the frame rate, the controller operates in some embodiments to change the intensity of the radiation beam or the radiation source is switched on or off as appropriate and as defined by one or a set of movement conditions. This allows tailoring the modifying or generating of the radiation beam to different phases of the intervention or to different types of devices (such as catheter and guidewires) or to different (anatomic or otherwise) surroundings inside the object.

Increasing or decreasing the radiation intensity can be effected by either increasing or decreasing the voltage and/or amperage of the radiation source. Preferably it is the amperage that is changed and not the voltage. In one embodiment, instead of switching the radiation source on or off, it is the collimator that is controlled so as to open the aperture or close the aperture. In other words, in this embodiment, it is the blocking function of the collimator that allows or prevents the radiation beam to impact on the imager's detector.

According to one embodiment, the tracking image generating unit comprises the collimator for collimating the radiation beam, wherein the controlling of the tracking image generating unit's operation results in the beam traversing a region of the object that includes the introduction element.

Since the moving unit is adapted to provide a movement parameter or a stream of movement parameters, which define a movement of the introduction element within the object, to the tracking image generating unit, the tracking image generating unit knows the real physical movement of the introduction element, which can be used by the controller for controlling the tracking image generating unit such that the radiation beam traverses a region of the object that includes the introduction element. This control of the radiation beam can be performed very accurately based on the known real physical movement of the introduction element such that it is not necessary to irradiate a relatively large area of the object for ensuring that the introduction element is really captured by the tracking images, thereby allowing for a reduced radiation dose applied to the object.

Preferentially, the movement parameters define a movement of the tip of the introduction element within the object, wherein the controller is adapted to control the tracking image generating unit depending on the provided movement parameters such that the radiation beam traverses a region of the object that includes the tip of the introduction element.

The introduction element is preferentially a catheter, a needle or another interventional instrument to be introduced into the object, which is preferentially a living object like a person or an animal. The moving unit is preferentially a robot for robotically moving the introduction element within the object, wherein this robotical movement can be controlled automatically (that is, without user interaction) or by a user like a physician, who may (remote-)control the moving unit via an input unit like a keyboard, a joystick, a touch screen, a mouse, et cetera. The tracking image generating unit is preferentially adapted to generate a sequence of tracking images showing the introduction element, while it moves within the object. Preferentially, the tracking image generating unit is adapted to generate x-ray images showing the introduction element within the object. The tracking image generating unit is, for instance, an x-ray C-arm unit.

According to one embodiment, the tracking image generating unit comprises a collimator for collimating the radiation beam, wherein the controller is adapted to control the collimator such that the radiation beam is collimated depending on the provided movement parameters such that the radiation beam traverses a region of the object that includes the introduction element. The controller may be adapted to control the collimator depending on a speed of the movement as defined by the movement parameters and/or a response time of the interventional system. In particular, the controller can be adapted to control the collimator depending on the speed of the movement as defined by the movement parameters and/or the response time of the interventional system such that a part of the radiation beam, which is in front of the introduction element with respect to a movement direction defined by the movement parameters, increases with increasing speed and/or with increasing response time.

Thus, the controller can be adapted to control the radiation beam by controlling the collimator of the tracking image generating unit. However, the controller can also be adapted to control other components of the tracking image generating unit for controlling the radiation beam like the radiation source and the radiation detector of the tracking image generating unit. For instance, the controller can be adapted to control the positions of these components for providing a desired direction of the radiation beam.

In a preferred embodiment the interventional system further comprises an identification unit for identifying the introduction element in the generated tracking images, wherein the controller is adapted to control the tracking image generating unit depending on the identification of the introduction element in the generated tracking images. Thus, not only the movement parameters may be used for controlling the tracking image generating unit, but also the identification of the introduction element in the generated tracking images. The identification of the introduction element in the generated tracking images is indicative of the real physical position of the introduction element within the object. Using this information regarding the real physical position of the introduction element within the object obtained from the tracking images together with the movement parameters provided by the moving unit for controlling the tracking image generating unit, in particular, the radiation beam, further improves the quality of tracking the introduction element by using the tracking images. For instance, the identification of the introduction element in the tracking images can be used to control the direction of the radiation beam, for example, the radiation beam can be controlled such that the introduction element, in particular, the tip of the introduction element, is centrally located within the tracking images, wherein the width, or shape or cross-section of the radiation beam can be controlled depending on the movement parameters.

The identification unit is preferentially adapted to use known segmentation algorithms for segmenting the introduction element in the generated tracking images, in order to identify the introduction element. In other words, using the real physical position as captured by the tracking image or images allows operation of the system in "hot" tracking mode in distinction to a cold tracking mode as explained earlier above.

The interventional system may further comprise a position determination unit for determining the position of the introduction element within the object based on the movement parameters, wherein the controller can be adapted to control the tracking image generating unit depending on the determined position of the introduction element. Moreover, the tracking image generating unit may comprise a collimator for collimating the radiation beam, wherein the position determination unit can be adapted to additionally determine an accuracy value being indicative of the accuracy of the determination of the position and wherein the controller can be adapted to control the collimator depending on the accuracy value. This allows controlling the tracking image generating unit during a switch off period, in which the tracking image generating unit temporally does not generate tracking images. If at the end of the switch off period the tracking image generating unit is switched on again, the generated tracking images immediately show the introduction element, even if the introduction element has been moved during the switch off period.

Preferentially, the controller is adapted to control the collimator such that the collimator has a narrower opening or aperture, if the accuracy value indicates a higher accuracy, and that the collimator has a wider opening, if the accuracy value indicates a lower accuracy. The accuracy value may be determined depending on, for instance, the speed of the movement defined by the movement parameters and/or depending on the total amount of movement defined by the movement parameters during a switch off period. The total amount of movement may be defined as being the total distance that the introduction element has traveled during the switch off period.

The interventional system may further comprise a) a position determination unit for determining the position of the introduction element within the object based on the movement parameters, b) an object image providing unit for providing an object image showing the object, and c) a display for displaying the object image and a representation of the introduction element at the determined position of the introduction element in the object image. The object image can be an overview image showing a larger part of the object. For instance, the object image can be a roadmap image showing a vessel tree of a person, wherein the introduction element may be moved within a vessel of the vessel tree. Since the position of the introduction element within the object is determined based on the movement parameters, wherein a representation of the introduction element at the determined position of the introduction element in the object image, for instance, in the roadmap image, is shown on the display, the position of the introduction element within the object can be shown on the display, even if currently a tracking image is not generated. For instance, the location of tip of an introduction element can be shown within a roadmap image, even if a tracking image is currently not generated.

The interventional system may also comprise a) an object image providing unit for providing an object image showing the object, b) an overlay image determining unit for determining an overlay image being an overlay of the object image and the target image, and c) a display for displaying the object image and the tracking image overlaid on each other. The object image can be, for instance, a roadmap image showing a vessel tree of a person. Since the tracking image shows the introduction element, by displaying the object image and the tracking image overlaid on each other, the position of the introduction element within the object can be shown to a user. Also in this embodiment the object image is preferentially an overview image showing a larger part of the object.

In another aspect of the present invention an interventional method is presented, wherein the interventional method comprises:

moving an introduction element within an object by a moving unit, generating tracking images of the introduction element within the object by a tracking image generating unit, wherein a radiation beam for traversing the object is emitted by a radiation source of the tracking image generating unit and wherein the radiation beam is detected after having traversed the object by a radiation detector of the tracking image generating unit, wherein the moving unit provides movement parameters, which define a movement of the introduction element within the object, to the tracking image generating unit and wherein a controller controls the tracking image generating unit depending on the provided movement parameters such that the radiation beam traverses a region of the object that includes the introduction element.

According to one embodiment, the movement parameter records a speed of the introduction element as experienced during the movement and/or a distance traveled by the introduction element during the movement. In some embodiments, the movement parameter records the direction of travel and speed (velocity). Speed/velocity may be recorded as the maximum speed in a time interval or as an average over a time interval or as instantaneous speed/velocity.

According to one embodiment, the movement condition includes any one or a combination of i) movement of the introduction element by at least a pre-defined distance and/or ii) movement of the introduction element at a speed in excess or less than a speed threshold.

In sum and as will be understood from the above embodiments, the robot control operations of the user (for instance joystick actuation events) in and of themselves are not what affects the beam control but beam control is responsive only to whether the actual motion (as captured in the movement parameter) of the catheter fulfills the movement condition.

It shall be understood that a preferred embodiment of the invention can also reside in any combination of the dependent claims or above embodiments with the respective independent claim.

These and other aspects of the invention will be apparent from and elucidated with reference to the embodiments described hereinafter.

Definitions

"Radiation source switched on/is triggered: radiation leaves the source to irradiate the object and an image is acquired;
"Radiation source switched off": no image is acquired;
"Radiation source is enabled": imager (in particular radiation source or detector) is ready for image acquisition;
"Radiation source is disabled": radiation source (in particular radiation source or detector) is not ready for image acquisition;
"Screen/display/monitor are used interchangeably herein;
"Tracking image generating unit" and "imager" are used interchangeably herein.

BRIEF DESCRIPTION OF THE DRAWINGS

Exemplary embodiments of the invention will now be described with reference to the following drawings wherein.

DETAILED DESCRIPTION OF EMBODIMENTS

Figure 1:
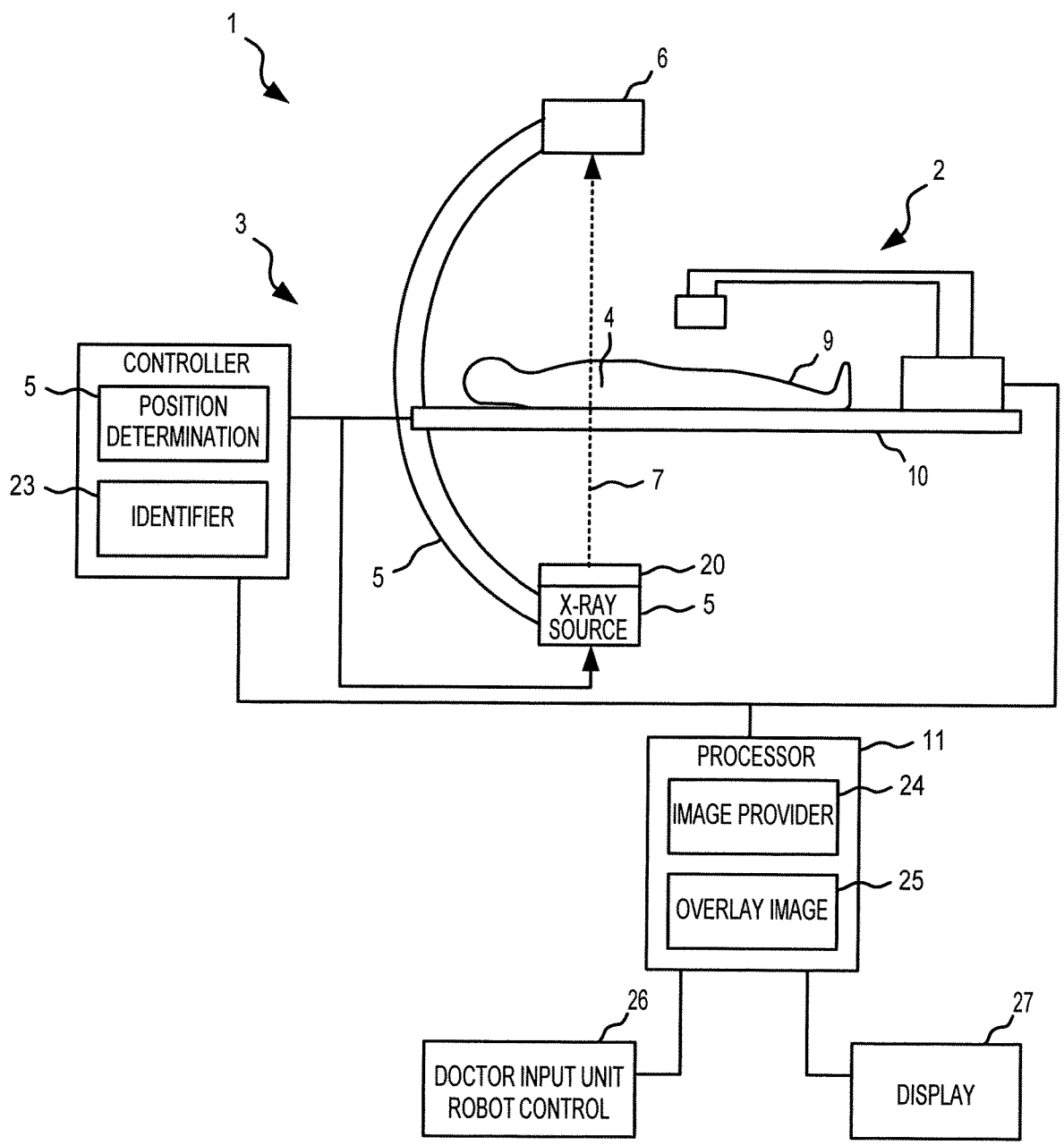
FIG. 1 shows schematically a block diagram of an interventional system.

FIG. 1 shows schematically and exemplarily an embodiment of an interventional system. In this embodiment, the interventional system is a catheter system 1 for introducing a catheter 4 into a person 9 lying on a support means like a patient table 10.

The catheter system 1 comprises a moving unit 2 for moving the catheter 4 within the person 9. In this embodiment, the moving unit 2 is a robotic unit for robotically moving the catheter 4 within the person 9. The robotic unit 2 is controlled by a user like a physician via an input unit 26. The input unit 26 may comprise a joystick, a keyboard, a mouse, a touchpad or another means for allowing the user to control the movement of the robotic unit 2.

The movement performed by the robotic unit 2 can be described by movement parameters, which may define a sequence of positions of the catheter 4, particularly of the tip of the catheter 4, within the person 9, and by corresponding time stamps such that for each position the respective time is known. The movement parameters are transferred from the robotic unit 2 to a tracking image generating unit 3 ("imager").

The tracking image generating unit 3 is adapted to generate several tracking images, which correspond to different times and which show the catheter 4, particularly the tip of the catheter 4, at different positions during the movement. In this embodiment, the tracking image generating unit 3 is an x-ray C-arm system comprising an x-ray source 5 emitting an x-ray radiation beam 7 for traversing the person 9 with the catheter 4. The x-ray C-arm system 3 further comprises an x-ray detector 6 for detecting the radiation beam 7 after having traversed the person 9 with the catheter 4, and a controller 8 for controlling operation of the imager 3. In particular it is the radiation beam 7 that is controlled for generating x-ray projection images based on the radiation detected by the x-ray detector 6, wherein the generated x-ray projection images, i.e. the generated tracking images, show the catheter 4, particularly the tip of the catheter 4, within the person 9 at different positions during the movement, i.e. several tracking images are generated, which correspond to different times during the movement of the tip of the catheter 4 within the person 9. The images can be a displayed on a display unit 27 such as a monitor. Control of the beam 7 is effected by controlling the imager's 3 collimator and/or the x-ray source 5. In short, controller 8 operates to modify or generate radiation beam 7. The control operation is based on certain movement parameters as explained in more detail below.

The imager's collimator 20 allows collimating the radiation beam 7, wherein the controller 8 is adapted to control the collimator 20 such that the radiation beam 7 is collimated depending on the provided movement parameters such that the radiation beam 7 traverses a region of the person 9 that includes the catheter 4, particularly the tip of the catheter 4. For instance, the controller 8 can be adapted to control the collimator 20 depending on the speed of the movement as defined by the movement parameters and/or a response time of the interventional system. In particular, the controller 8 can be adapted to control the collimator 20 depending on the speed of the movement as defined by the movement parameters and the response time of the interventional system 1 such that a part of the radiation beam 7, which is in front of the tip of the catheter 4 with respect to a movement direction defined by the movement parameters, increases with increasing speed and with increasing response time. The part of the radiation beam in front of the tip of the catheter 4 with respect to the movement direction defined by the movement parameters can be regarded as defining a safety margin. Since the movement parameters are used for controlling the safety margin, the safety margin can be smaller than a safety margin, which has to be used by a tracking image generating unit with a standard tight collimation technique as described in the above mentioned patent document WO 2005/009243 A1. The safety margin, i.e. in this example the part of the radiation beam in front of the tip of the catheter 4 with respect to the movement direction defined by the movement parameters, may be defined by following equation:

$$S > vt_r \qquad (1)$$

wherein S represents the safety margin in front of the tip of the catheter 4, v represents the speed in the movement direction, i.e. the corresponding speed set point of the robotic unit 2, and $t_r$ represents the response time of the interventional system.

The safety margin S and the speed v relate to quantities in the tracking images, i.e. S is a length in front of the tip of the catheter in the movement direction and v is the speed of the robotic unit as defined by the movement parameters with respect to an image reference frame defined by the tracking images, wherein the movement parameters, i.e. the velocity v defined by the movement parameters, have been transformed to correspond to the reference image frame. A transformation, which can be used for transforming the movement parameters to the image reference frame, is described further below.

The response time of the interventional system is preferentially defined as being the time between an action of motion of the introduction element within the person 9 and a control of the radiation beam in reaction of the action of motion. This response time depends on, for instance, the latency between the moving unit and the controller, the time needed by the collimator to react on inputs from the controller, time needed by an identification unit 23 to identify catheter in the tracking image et cetera.

The identification unit 23 can identify the catheter 4 in the generated tracking image and the controller 8 can control the radiation beam 7 such that the identified catheter 4 is centrally located or at another position within the tracking image. The identification unit 23 can use known segmentation algorithms for identifying the catheter 4 within the tracking images. The collimation, i.e. the width, shape or cross-section of the radiation beam 7, can be determined based on the movement parameters, for instance, based on the speed of movement as defined by the movement parameters as described above. In other words, using the real physical position as captured by the tracking image or images allows operation of the system in "hot" tracking mode in distinction to a cold tracking mode as will be explained in the following.

The interventional system can further comprise a position determination unit 22 for determining the position of the catheter 4, particularly of the tip of the catheter 4, within the person 9 based on the movement parameters, wherein the position determination unit 22 can be adapted to additionally determine an accuracy value being indicative of the accuracy of the determination of the position. This determined position and accuracy value is preferentially used for controlling the tracking image generating unit 3, if the tracking image generating unit 3 temporally does not generate tracking images, i.e. if the tracking image generating unit 3 is in a switch off period and the system operates in "cold" tracking mode. This control is preferentially performed such that, if the generation of the tracking images is started again, the tracking images immediately show the tip of the catheter 4. Moreover, the control is preferentially performed such that the collimator 20 has a narrower opening defined by one or more movable collimator shutters, if the accuracy value indicates a higher accuracy, and that the collimator 20 has a wider opening, if the accuracy value indicates a lower accuracy. The position determination unit 22 is preferentially adapted to determine the accuracy value depending on the speed of the movement defined by the movement parameters during the switch off period and/or the total amount of movement defined by the movement parameters during the switch off period, wherein with increasing speed and/or increasing total amount of movement, respectively, the accuracy value decreases. The accuracy value can also be a function of the switch off time, wherein with increasing switch off time the accuracy value may decrease. The accuracy value may also depend on results from calibration steps performed for calibrating the interventional system. For instance, during a calibration procedure the accuracy of determining the position of the introduction element within the object based on the movement parameters can be determined by determining this position several times based on the same movement parameters, wherein the accuracy can be estimated depending on the resulting distribution of determined positions. For example, the accuracy value can be determined depending on the standard deviation of this distribution.

Thus, when operating in cold tracking mode, the interventional system allows estimating the location of the catheter 4, even if the x-ray source 5 is switched off. The location of the catheter 4 can be determined based on the movement as defined by the movement parameters and based on a known location of the catheter, from which the catheter 4 has been moved away. This known location can be a location, which has been determined by using a tracking image and by identifying the catheter 4 in the tracking image. If the x-ray source 5 is temporally switched off, this location of the catheter 4 determined by using the movement parameters can be used to control the components of the tracking image generating unit 3 defining the direction and shape of the radiation beam like the collimator 20 such that they follow the estimated location of the catheter 4. If then the x-ray source 5 is switched on again, the tracking image will capture the catheter 4 already very well, wherein the capturing of the catheter 4 can then be refined based on the generated tracking image.

In this embodiment the controller 8 comprises the position determination unit 22 and the identification unit 23. However, in another embodiment these units can also be arranged in another part of the interventional system 1, for instance, in another processing unit like the processing unit 11, which in this embodiment comprises an object image providing unit 24 for providing an object image showing the person 9. The object image providing unit 24 is adapted to provide an overview image preferentially including roadmap information showing vessels along which the catheter 4 can be moved within the person 9. The object image providing unit 24 is therefore preferentially adapted to provide a roadmap image. The roadmap image can be shown together with a representation of the tip of the catheter 4 at the position determined by the position determination unit 22 on the display 27, in order to allow a user like a physician to know the position of the tip of the catheter 4 within the person 9, even if the tracking image generating unit 3 does not provide actual tracking images, because, for instance, the radiation source 5 is switched off. The representation shown on the display 27 at the determined position of the tip of the catheter 4 can have the shape of a projection of the tip of the catheter 4 or it can have another shape. For instance, it can be circular, quadratically, et cetera. The catheter can therefore be blended in or artificially drawn into the provided object image.

The provided object image is preferentially an overview image that ensures that the user keeps a sense of the surrounding area. It can be a pre-acquired image, which may have been generated by the tracking image generating unit 3 or by another image generating device like a computed tomography imaging device, a magnetic resonance imaging device, et cetera. If the object image is a pre-acquired image, which has been generated by the tracking image generating unit 3, it may be an exposure or cine image or a fluo image. The exposure or cine image is generally generated by using a higher x-ray dose, after a contrast agent has been injected into the person, in order to generate a low noise image showing, for instance, a vessel tree. The fluo image is a noisier lower dose image. The exposure or cine image is preferred in comparison to the fluo image, because of the reduced noise.

The interventional system further comprises an overlay image determining unit 25 for determining an overlay image being an overlay of the object image and a target image 1035. Since the catheter 4 is shown in the target image, by showing an overlay image being composed of the object image, which is preferentially an overview image showing the surrounding area, and the target image showing the catheter 4, the position of the catheter 4 in relation to the surrounding area within the person 9 can be shown to the user.

According to one embodiment, controller 8 is further configured or is configured instead to switch on or off the x-ray source 5. The switching on or off operation depends on whether the movement parameters fulfill the user definable movement condition. In other words, controller 8 operates to trigger (switch on) an exposure of the object to x-ray radiation to acquire a tracking image or operates to switch off the x-ray source so that no tracking image is acquired. It will be understood herein that the switching operation does not necessarily mean that the x-ray source 5 is powered on or off. For instance, in one embodiment the on-off operation is effected by switching on-off a grid to block electrons (discharged from the x-ray source 5's cathode) from reaching the x-ray source 5's anode. In one embodiment, instead of switching on/off the radiation source, it is the collimator 20's aperture that is opened/closed, respectively.

According to one embodiment it is envisaged herein that controller 8 operates to switch on the x-ray source 5 whilst the system operates in cold tracking mode, when the position determination unit has registered that a pre-determined movement condition has been fulfilled. For instance, the movement condition may specify a certain distance. If the position determination unit then determines from the received movement parameter that the distance traveled by the catheter 4 exceeds the predefined distance threshold, the controller then issues a trigger signal to switch on x-ray source 5 to acquire a new tracking image. The identification unit can then determine a new, updated actual position. This allows "reality checking" the kinematic estimations or predictions of the position determination unit 22 and, if need be, the application of a correction of the position of the indicator in the roadmap image. This allows the user to continue navigating based on the roadmap image alone although the x-ray source 5 is switched off. In one embodiment, when operating in cold tracking mode, the controller issues a trigger command to switch on the x-ray source to acquire a single tracking image when the position determination unit 22 registers that the provided movement parameter fulfils the movement condition. Preferably, each time a movement parameter fulfills the condition, x-ray source 5 is triggered for a single exposure. This cold tracking operation of the imager with automatic x-ray exposure control would appear to an observer as if the x-ray source operates every now and then with single exposures as the user remote controls the robotic unit to navigate the catheter through the patient 9.

According to one embodiment there is a user operable trigger mechanism to switch on the x-ray source 5 to effect exposure or tracking image capture. According to one embodiment the trigger mechanism is a pedal. If the user wishes to acquire an image, he or she depresses by foot operation the pedal to issue a request for image acquisition at the desired instant. Suitable event handlers intercept the pedal action event and forward a suitable trigger command to the x-ray source 5. The x-ray source 5 then responds to this trigger command by emitting the x-ray beam.

In one embodiment, the controller operates 1036 to "guard" the patient against undue over dosage by blocking the trigger command if the position determination unit 22 registers that the received movement parameter does not fulfill a predefined movement condition. For instance, in one embodiment the position determination unit 22 examines whether the received movement parameter records that a movement has taken place or that certain minimum distance has been traveled and/or that the movement occurred at predefined speed and/or that a certain minimal time has passed between last acquisition. If, on the other hand, the user request for image acquisition is received and it is determined that the movement condition is fulfilled, the request and or the trigger command is forwarded (so controller's blockage of the request ceases) to the x-ray source 5 so that exposure can be effected. This effectively means that it is still always the user who is in control as to aborting an image acquisition because in this case users simply take their foot off the pedal to abort exposure. In other words, the imager 3 is enabled (and not disabled), but the triggering of the radiation source is only effected if the movement parameter fulfills the movement condition. However, in one embodiment the system provides further input means so that the user can override the blocking operation by the controller and so still effect exposure although the movement condition is not fulfilled. For instance, to override the controller 8's blocking mode, the user is to press an "override button" or a similar actuator at the same time when actuating the foot pedal.

According to one embodiment the controller 8 further operates to change the frame rate 1034 of the x-ray source 5 in dependence on the movement parameter fulfilling the predetermined movement condition.

For instance, in one embodiment position determination unit 22 examines the received movement parameter for speed and/or velocity at which the catheter 4 has been advanced. If it is determined that the robot unit has operated in a "high velocity mode" (that is, at a velocity higher than a threshold speed specified in the condition), it is reasonable to assume that no detailed imagery is required at this stage, so correspondingly the x-ray operation is either switched off or it operates at a relatively low frame rate of about less than 15 fps or operates to emit a beam 7 of lesser intensity. Again, as in the previous embodiments a suitable movement condition (or "protocol") can be defined and the movement parameters can be interrogated whether the velocity or speed information encoded in the movement parameter does fulfill the condition. If however it is found that the robotic unit operates in a "low velocity mode" (that is at a speed less than a predefined threshold speed specified in the condition) it is reasonable to assume that the user is carefully navigating his or her way to a target so more detailed imagery of the surroundings is called for. In other words, in this low velocity mode the x-ray source is switched on to operate at a relatively high frame rate, for instance at 15 fps or more.

According to another embodiment, the frame rate is set in dependence on the direction of movement as recorded in the received movement parameter. For instance position determination unit 22 examines the movement parameter as to whether the motion occurred in forward or backward direction, that is, whether the robotic unit has been operated to move the catheter further inside ("forward") the patient's body 9 or whether the catheter 4 has been moved in a direction along the traveled path that, if followed, would take the catheter back to the entry point, that is, out ("backward") of the patient's body. Again, whether the recorded motion is "into" or "out" of the patient body 9 can be determined by examining the information in the movement parameter that encodes the direction as explained in more detail below.

According to one embodiment, if it is determined that the direction indicates a movement further into the patient's body, controller increases the frame rate because it can be assumed that the user still navigates towards the target region or region of interest. However if a reverse direction is detected, it can be assumed that the user wishes to remove the catheter from the patient's body, and therefore a low frame rate is set by the controller. This embodiment with low frame rate at reverse direction can be used in particular with the embodiment were roadmap images are used and displayed to provide the necessary information to the user for the navigation on the way out.

According to another embodiment, the frame rate is adjusted 1034 in accordance with the procedure workflow or stage/phase of the intervention. The procedural stage/phase can be defined or set either by user input, or by examining the movement parameter for the distance traveled and or the speed at which the movement occurred. Both distance and speed may indicate a different stage of the procedure, and the frame rate can either increase or decrease as appropriate.

In some interventions, different types of devices/catheters 4 are used at different times or phases. For instance, in an exploratory phase, a guide wire is usually introduced into the patient and navigated to the target structure. In a subsequent deployment phase, the catheter 4 is introduced into the body to slide along the path defined by the now resident guide wire. In the embodiment where different device types are used, or where the same device changes its appearance during the intervention, the identification unit 23 can be used to identify automatically the device type by segmentation of the respective tracking images and by using predefined silhouette profiles held in a database. Segmenting the tracking image for the respective profiles can be used to identify the different device 4 footprints as recorded in the tracking images. Referring back to the guide wire-catheter example, once the identification unit 23 has identified that it is the guide wire that is currently used, a higher frame rate is set as compared to the deployment phase where the path is already known. In other words in the deployment phase where the identification unit 23 identifies the profile of the catheter, x-ray source operates at a lower frame.

As will be appreciated by those schooled in the art, the different settings of the frame rate are chosen so as to maximize the information available to the user for the purpose of safe navigation but to still keep the dosage on the patient as low as possible. According to one embodiment, the system provides input means for the user to override the frame rate set by the controller. In other words, although the controller decides for a low frame rate, the user can still increase same. It will also be appreciated herein, that the previous frame rate adjusting embodiments can be used either alone or in combination with the other embodiments.

It should also appreciated that the operation of the controller to switch on or off the x-ray source or to change the frame rate of the x-ray source or to change the beam's intensity may operate independently of the controller's collimator adjustment operation. For instance, according to one embodiment, controller 8 operates to switch on/off the source or adjusts the frame rate of the x-ray source or adjusts the beam intensity but does not adjust the collimator. In a preferred embodiment however the controller controls both, the collimation and the operation of the x-ray source. The control operations of collimation control and x-ray source control (on/off, frame rate, intensity) may be executed by a single controller, or there is a dedicated, distinct controller for each operation. In one embodiment, the dedicated controllers are integrated into one controller. In other words, the imager 3 "controller 8" as used herein may include a plurality of different controllers, one for each control operation (x-ray source adjustment (on/off, frame rate, intensity) and collimator adjustment).

In all embodiments, the movement parameters record the actual motion experienced by the catheter 4 as it is moved by robotic unit 2. How exactly the movement parameters are gotten depends on the functioning of the robotic unit 2's actuator circuitry.

For instance, determining the movement parameters may depend on the types of actuators used in the robotic unit 2, the motion of the actuator's movable parts (piston, rotor, nut on a screw etc) and the gearing used. Data that specify gearing ratios and the movement of the movable parts in robotic unit 2's actuator are programmed into an interface module or "middleware" (arranged between robotic unit 2 and controller 8).

The interface module or middleware is run by position determination unit 22. The middleware uses sensors or event handlers to intercept control commands or signals as generated in the robotic unit during motion of the movable parts when catheter 4 is moving. Position determination unit 22's middleware then operates to translate the intercepted commands and signals into an actual distance traveled and/or speed and/or direction of movement of the catheter 4.

More specifically and according to one embodiment, position determination unit 22 operates to establish a forward or backward direction of the catheter movement with respect to an entry/ingress point into the patient 9 or with respect to a target structure in patient 9. According to one embodiment, position determination unit 22's middleware interfaces with robotic unit 2 via suitable sensors or by examining commands as generated by the robotic unit during its operation to establish an orientation for the movement of the catheter 4 caused by the robotic unit. For instance, the robotic unit, to cause motion of the catheter 4, may use linear actuators with moving parts. Non-limiting examples of moving parts in actuators are: rotors in a stepper motor arrangement, pistons in a hydraulic arrangement, or threaded shafts in a ball screw arrangement. The orientation of the motion of the moving parts can be used to determine the nature of the movement that the payload (in this case the catheter 4) experiences. Provided the gear train between actuator and catheter 4 is known, orientation of the motion of said moving parts can be translated into a forward or backward motion of the payload 4. For instance, in a ball screw arrangement, the orientation of the rotation (left, right) of ball screw's threaded shaft can be translated not only into the distance traveled by the nut (moving along said shaft) and the speed of the nut, but also whether the nut moved forward or backward along the shaft.

In some embodiments, the movement parameters such as distance traveled, speed and orientation of movement (forward, backward) can be obtained by a more "high level" approach, for instance by examining the semantics of the control commands generated in the robotic unit. The control commands will encode this information in one form or another. For instance, there will be a specific symbology that encodes the distance, speed, orientation for any one command that causes a kinematic event that affects the motion or position of the catheter 4. The event may be stored as a typical bit pattern etc in a registry of the robot's 2 circuitry.

In one embodiment, there are also confirmation signals generated in the circuitry of the robot 2 that confirm that a movement has successfully terminated. In other words, the movement parameter can be obtained by programming the position determination unit 22's middleware to "understand" and translate the semantics of the control commands and can be programmed to listen for said command and the associated confirmation signals.

For each type of intervention, a number of different movement conditions can then be defined either on the fly during the invention or in a preparatory phase prior to the intervention. For instance, the system in one embodiment invites the user to input the movement conditions that the controller 8 is to observe when controlling operation of the imager 3 in particular its x-ray source 5 (or the collimator 20 as explained earlier above).

The movement conditions include a specific distance traveled or an interval for a distance, or a speed threshold or interval. In one embodiment, user input of movement condition is via keyboard or via a graphical user interface (GUI) brought up on monitor 27 or on a different monitor. User can provide the input by filling-in GUI fields or boxes or by mouse clicking on GUI widgets, or selecting drop-down menu items etc.

Using an actual position of the catheter 4 as confirmed by the identification unit 23 in a tracking image and a distance traveled as recorded in the movement parameter allows defining a specific position or location or range of positions within the object 9 where the catheter resides. In other words, the confirmed position as provided by identification unit 23 is used as an initial condition (in the kinematic sense) and the distance traveled as obtained by the position determination unit 22 is added (vectorially) thereto to so arrive at the catheter position within the object. In general it is a sequence or stream of movement parameters that is generated during operation of the imager and that the position determination unit 22 compares the stream of movement parameter against one or more movement conditions to flag up an event when a movement parameter is received in the stream that does fulfill the condition.

Figure 2:
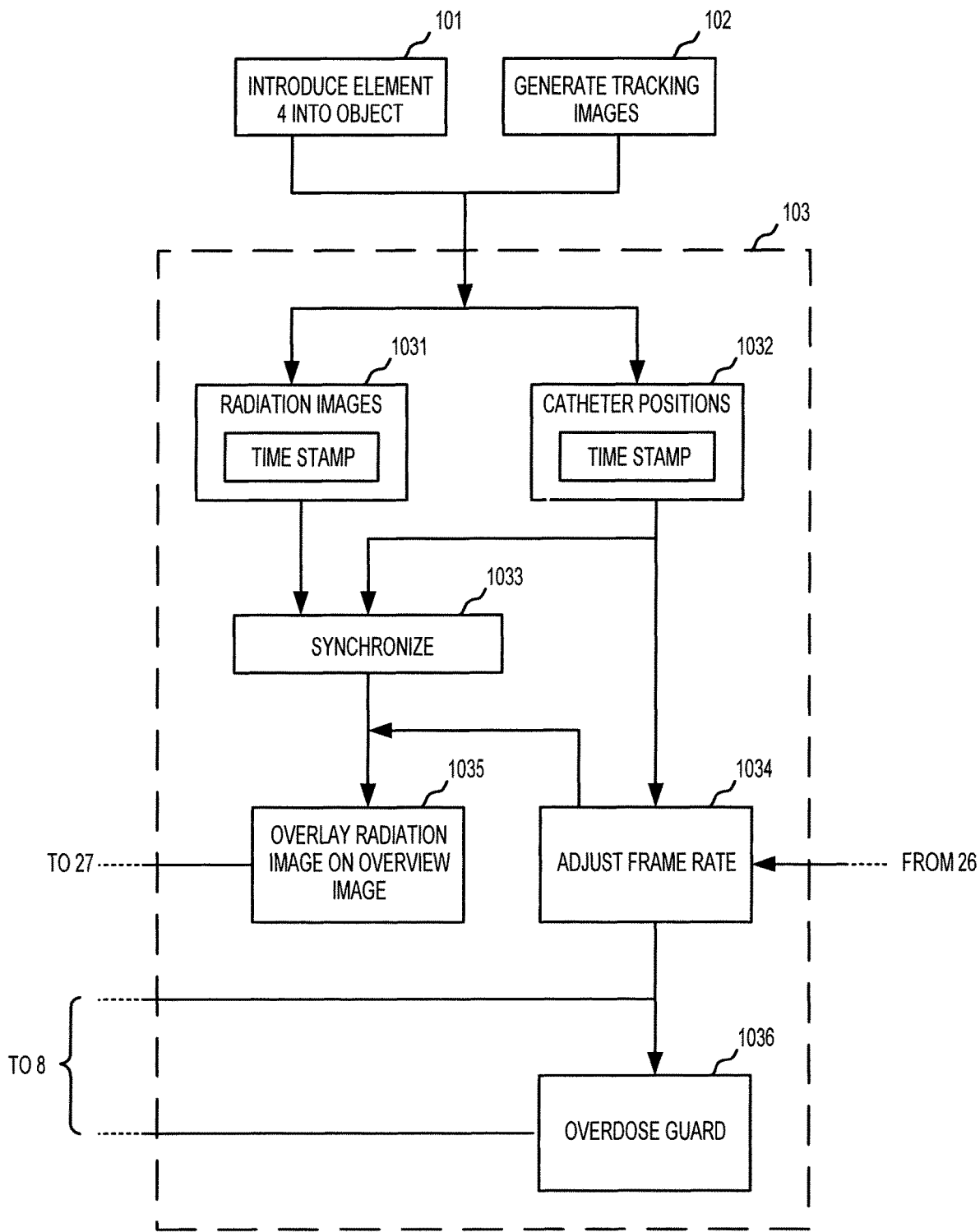
FIG. 2 shows a flowchart for an interventional method.

In the following an embodiment of an interventional method will exemplarily be described with reference to a flowchart shown in FIG. 2.

In step 101 an introduction element 4, which is introduced into an object 9, is moved by using a moving unit 2. In particular, a catheter 4 is moved within the person 9 by using the robotic unit 2 in accordance with an input into the robotic unit 2 provided by a user via the input unit 27.

In step 102 during the movement of the introduction element 4 within the object 9, one or more tracking images of the introduction element 4 within the object 9 are generated by a tracking image generating unit 3, wherein a radiation beam 7 for traversing the object 9 is emitted by a radiation source 5 of the tracking image generating unit 3 and the radiation beam 7 is detected after having traversed the object 9 by a radiation detector 6 of the tracking image generating unit 3 for generating a tracking image.

In step 103 the radiation beam 7 is controlled by a controller 8, wherein the moving unit 2 provides movement parameters, which define a movement of the introduction element 4 within the object 9, to the tracking image generating unit 3 and wherein the controller 8 controls the imager, in particular, controls the radiation beam 7 depending on the provided movement parameters such that the radiation beam 7 traverses a region of the object 9 that includes the introduction element 4. In one embodiment, the controller operates to control the collimator so that the collimated beam appears "to follow" the catheter 4 during the catheter movement caused by the robot 2. Providing of the movement parameter may be either direct to the tracking image generating unit 3 or may be routed indirectly via a computing unit to the tracking image generating unit 3.

According to one embodiment, in addition or instead of controlling the collimator, it is the x-ray source 5 that is controlled in step 103 by the controller 8 or by a further controller.

More specifically in one embodiment, the x-ray source 5 is switched on (that is, an exposure is triggered) or is switched off in response to the movement parameter that records a movement of the introduction element caused by the robotic unit as of step 101. More specifically, an exposure (that is, a tracking image acquisition) is triggered if it is determined that the movement parameter fulfills a pre-defined movement condition.

The movement condition may define, according to one embodiment, the distance traveled (introduction element) or the speed (or velocity) with which introduction element has been moved by the robotic unit or may define any other suitable kinematic event (such as rotation, with or without orientation, the direction of travel, etc).

According to one embodiment, in step 103 a frame rate of the x-ray source is controlled 1034, that is, the frequency at which individual x-ray tracking images are acquired by the x-ray source. The frame rate may be likewise controlled in dependence on certain kinematic events and whether or not those events fulfill the predefined movement condition. However, in other embodiments the frame rate is controlled in dependence on the type of the introduction element and or a phase of the interventional procedure.

It is understood herein that the order of steps 102,103 may be reversed in some embodiments, in other words step 102 may not necessarily occur before step 103. For instance, during cold tracking no image is acquired but imager 3 is controlled as of step 103, that is, the image acquisition in step 102 occurs after it is determined in step 103 whether the movement condition is fulfilled. Control of collimator and x-ray source may not necessarily be done both or may not occur concurrently. In some instances, it is only the collimator that is controlled in step 103, or it is only the x-ray source that is controlled. In some instances, both, x-ray source and collimator are controlled, either concurrently or sequentially.

In one embodiment, in step 103 the controller controls the radiation beam 7 also depending on the position of the introduction element 4 within the tracking image generated in step 102.

Steps 101 to 103 are preferentially performed in a loop, wherein the controller 8 controls the radiation beam 7 such that the introduction element 4, in particular, the tip of the introduction element 4, is centrally located in the tracking images and such that the collimation, i.e. the width, of the radiation beam 7 is determined depending on the movement parameters received from the moving unit 2.

The procedure in accordance with step 103 can be regarded as defining a controlling method for controlling a tracking image generating unit, specifically, a radiation beam used by the tracking image generating unit of an interventional system, wherein the controlling method comprises controlling the radiation beam 1036 based on movement parameters provided by the moving unit of the interventional system. The effect of this control operation is generation or modification of the imager's 3 radiation beam based on events recorded in the movement parameter. For instance, the beam may be so controlled/modified that it traverses a region of an object that includes the introduction element. In other embodiments the radiation beam is switched on/off or has its intensity changed or has its frame rate changed. Instead of switching the beam on/or off the controller may open/close the collimator's aperture.

Minimizing both staff and patient radiation dose 1036 for a given clinical procedure is a competitive issue in interventional x-ray procedures. In order to reduce these radiation doses, the above mentioned patent document WO 2005/009243 A1 discloses a tight collimation technique that automatically detects relevant regions of interest (ROIs) in technical images and that tries to limit the extent of the x-ray radiation beam as much as possible to only the ROI. By using this tight collimation technique, the dose area product can be reduced by reducing the irradiated area. The tight collimation technique uses image analysis algorithms for defining clinically relevant ROIs at any step of the interventional procedure. The image analysis algorithms can further be adapted to define safety margins around the clinical relevant ROIs, in order to take into account sudden movements of an interventional instrument like a catheter due to, for example, sudden movements performed by the physician.

If the tight collimation technique would be used, without considering the movement parameters provided by the moving unit 2, as described in the above mentioned patent document, the safety margin would need to be larger than the largest distance the introduction element can travel between consecutive frames, i.e. between consecutive tracking images 1031 generated by the tracking image generating unit 3. The corresponding region can be relatively large, for instance, it can cover an area being up to five times larger than the area of the clinically relevant ROI. This would lead to a relatively large radiation dose, even if the tight collimation technique is used. Furthermore, if the tight collimation technique would be used without considering the movement parameters provided by the moving unit 2 and if the x-ray source would be switched off momentarily, the interventional system would not know to which location the catheter has been moved and, thus, the interventional system would need to control the collimator such that its shutters are opened completely, in order to reacquire the introduction element upon reassuming the fluoroscopy process, i.e. upon resuming the generation of the several tracking images for tracking the introduction element within the person. The interventional system described above with reference to FIG. 1 is therefore adapted to use the movement information from the robotic unit 2 to aid in the tracking of the introduction element with the tight collimation.

The movement parameters, which can define translational information, can be transferred from the robotic unit 2 to the tracking image generating unit 3 via a wired or wireless data connection. Besides the movement parameters, also further information may be transferred from the robotic unit 2 to the tracking image generating unit 3 or to the processing unit 11 like the kind of the catheter moved by the moving unit 2. The kind of catheter can be indicative of the actual phase of the interventional procedure performed by the interventional system. The transferred movement parameters can include information about the shape and therewith the orientation of the catheter, i.e. the movement parameters can include information about the direction in which the catheter is pointing. This direction is the moving direction, in which the catheter is actually moved.

Since there may be some latency in the complete link chains, the catheter system is preferentially adapted to synchronize 1033 the image information provided by the tracking images and the movement parameters, i.e. the movement information, provided by the robotic unit 2. This synchronization allows the controller 8 to "know", which image corresponds to which real physical movement defined by the movement parameters or to which real physical position of the catheter 1032, in particular to which real physical position of the tip of the catheter, as defined by the movement parameters. Preferentially, the controller 8 uses time stamps assigned to the sequence of real physical positions 1032 of the tip of the catheter 4 as defined by the movement parameters received from the robotic unit 2 and time stamps, at which the generated tracking images 1031 showing the tip of the catheter 4 during the movement have been acquired, for synchronizing the real physical positions of the tip of the catheter 4 as defined by the movement parameters provided by the robotic unit 2 with the acquisition times of the generated tracking images. In this way it can be known, which sets of data belong to each other. According to one embodiment said latency is also accounted for in the control operations of collimation control (opening/closing aperture) and x-ray source control (control on/off, control frame rate, control intensity).

The robotic unit 2 can be, for instance, the CorPath 200 from the company Corindus, the Magalan system from the company Hansen Medical or another robotic unit, which can be used for moving an introduction element like a catheter within an object, wherein the respective robotic unit is adapted to provide the movement parameters to the tracking image generating unit 3. The robotic unit can be adapted to allow the user, for instance, a physician, to control the introduction element with, for instance, a joystick from behind a lead screen, in order to reduce the radiation dose received by the user.

The controller 8 or a different controller can be adapted to convert the movement parameters obtained from the robotic unit 2 from a robot reference frame defined by the robotic unit 2 to an image reference frame defined by the tracking image generating unit 3. For performing this transformation corresponding transformation rules have to be determined, which relate the robot reference frame to the image reference frame. These transformation rules can be defined, for instance, by a calibration procedure, wherein positions and distances in the tracking images, i.e. in the image reference frame, are determined, while the corresponding positions and/or distances in the robot reference frame are known. This calibration can be performed pre-procedural, i.e. before the interventional procedure is performed, or during the interventional procedure, wherein in the latter case continuously catheter movements as input by the user into the robotic unit 2, i.e. corresponding positions and/or distances in the robot reference frame, are matched with corresponding changes visible in the tracking images. After the movement parameters have been transferred from the robot reference frame to the image reference frame, the above described determinations or calculations performed by the controller 8, which are performed for controlling the radiation beam depending on the movement parameters and depending on the identified introduction element identified in the tracking images, can be performed in the reference image frame.

The input from the robotic unit 2, i.e. the movement parameters, provided to the tracking image generating unit 3 can be used by the controller 8 for controlling the components defining the direction and the collimation of the radiation beam, if the radiation source 5 is switched off. This allows, for instance, the collimator, in particular one or several shutters of the collimator, to start moving in the right direction in accordance with the movement defined by the movement parameters, before the radiation source 5 is switched on again for acquiring a tracking image, thereby reducing the response time of the interventional system, which in turn can be used to reduce the safety margin 1036 in accordance with, for instance, equation (1).

The collimator 20 can be a standard collimator, in particular a standard symmetric collimator, as used in current x-ray C-arm systems. However, the collimator can also be a more complex collimator that allows for a more flexible control. For instance, the collimator may be a multileaf collimator, which may comprise multiple independently positionable leafs or shutter to effect more complex beam shapes.

Although in some of above described embodiments the controller is adapted to control the tracking image generating unit such that the tip of the introduction element is centrally located within the tracking images 1035, in other embodiments the tracking image generating unit can be controlled such that the tip of the introduction element is shown at another position within the tracking images. For instance, the tracking image generating unit can be controlled such that in front of the tip of the introduction element, i.e. in the direction of the movement of the introduction element in the image reference frame as defined by the transformed movement parameters that have been transformed to the image reference frame, the space within the tracking images is larger than behind the tip of the introduction element, i.e. larger than the space in the opposite direction, because it is more important for the user to have a visualization of the space, in which the tip of the introduction element is moved, than having a visualization of the space, from which the tip of the introduction element is moved away.

Although in the above described embodiments the tracking image generating unit is an x-ray C-arm system, in other embodiments the tracking image generating unit can also be another device for generating the tracking images, which comprises a radiation source for generating radiation traversing the object, a radiation detector for detecting the radiation, after it has traversed the object, and a controller for controlling the tracking image generating unit depending on movement parameters received from a moving unit for moving an introduction element within the object.

Although in above described embodiments the interventional system is a catheter system, in other embodiments the interventional system can also be another system adapted to perform an interventional procedure, wherein an interventional instrument is introduced into an object as the introduction element. For instance, instead of a catheter a needle can be used as the interventional instrument. In particular, the interventional system can be any interventional x-ray system.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Operations like the control of the radiation beam depending on the provided movement parameters, the determination of the position of the introduction element within the object based on the movement parameters, the determination of an accuracy value being indicative of the accuracy of the determination of the position of the introduction element, the identification of the introduction element in the generated tracking images, et cetera performed by one or several units or devices can be performed by any other number of units or devices. These operations and/or the control of the interventional system in accordance with the interventional method and/or the control of the radiation beam by the controller in accordance with the controlling method can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to an interventional system comprising an introduction element like a catheter for being introduced into an object, for instance, a person. A moving unit like a robot moves the introduction element within the object, wherein a tracking image generating unit generates tracking images of the introduction element within the object and wherein a controller controls the tracking image generating unit depending on movement parameters of the moving unit, which are indicative of the movement, such that the tracking images show the introduction element. This control can be performed very accurately based on the known real physical movement of the introduction element such that it is not necessary to, for instance, irradiate a relatively large area of the object for ensuring that the introduction element is really captured by the tracking images, thereby allowing for a reduced radiation dose applied to the object.

The invention claimed is:

1. An interventional system comprising:
   an introduction element for being introduced into an object,
   a robotic moving unit for robotically moving the introduction element within the object,
   a tracking x-ray fluoroscopic the tracking images generating unit for generating, using the radiation beam, a tracking image of the introduction element within the object, the tracking x-ray fluoroscopic image generating unit including an x-ray source and an x-ray camera configured to generate a series of time-stamped tracking images and being configured to start and stop generating the tracking images, increase or decrease a frame rate of the x-ray source, and increase or decrease an intensity of the radiation beam from the x-ray source, and
   a controller for controlling the tracking x-ray fluoroscopic image generating unit, including i) starting and stopping the x-ray source and ii) increasing or decreasing the frame rate of the tracking x-ray fluoroscopic image generating unit,
   wherein the robotic moving unit is adapted to provide a movement parameter to the tracking image generating unit,
   wherein the movement parameter defines a sequence of spatial positions of the introduction element within the object caused by the robotic moving unit, wherein the controller is further configured i) to convert the movement parameter from a robot spatial reference frame defined by the robotic unit to an image spatial reference frame defined by the tracking x-ray fluoroscopic image generating unit and ii) to control operation of the tracking x-ray fluoroscopic image generating unit in dependence on the provided movement parameter fulfilling a movement condition, wherein the robotic moving unit is further configured to provide time stamps corresponding to the sequence of spatial positions, and wherein the controller is further configured to use the time stamps assigned to the sequence of spatial positions and further time stamps representing an acquisition time of the tracking images for synchronizing the movement parameter provided by the robotic moving unit with the tracking images.

2. The interventional system as defined in claim 1, wherein the controlling by the controller includes a guard mode in which a user is blocked from switching on the x-ray source of the tracking x-ray fluoroscopic image generating unit in dependence on the movement parameter fulfilling a movement parameter.

3. The interventional system as defined in claim 2, wherein the controller is configured to cease, responsive to an override request, the blocking even though the movement parameter does not fulfill the movement condition.

4. The interventional system as defined in claim 1, wherein the interventional system further comprises a position determination unit for determining a position of the introduction element within the object based on a location of the object in one of the time-stamped tracking images and a vector describing a change in position subsequent to a position with a corresponding time stamp.

5. The interventional system as defined in claim 1, wherein the frame rate is increased or decreased in dependence on the determined position of the introduction element.

6. The interventional system as defined in claim 1, wherein the introduction element is introduced into the object through an ingress point and follows a path through the object, wherein the controlling of the tracking image generating unit includes decreasing the frame rate in dependence on the position determination unit registering that the introduction element is moved in backwards motion along said path in respect of said ingress point.

7. The interventional system as defined in claim 4, wherein the position determination unit is further configured to determine an accuracy value indicative of an accuracy of the determined position.

8. The interventional system as defined in claim 4, wherein the frame rate is increased upon the position determination unit registering that the introduction element is within a pre-defined distance of the target in the object.

9. The interventional system as defined in claim 1, wherein the movement parameter records a speed of the introduction element as experienced during the movement and/or a distance traveled by the introduction element during the movement.

10. The interventional system as defined in claim 1, wherein the movement condition includes any one or a combination of i) movement of the introduction element by at least a pre-defined distance and/or ii) movement of the introduction element at a speed in excess or less than a speed threshold.

11. An interventional system comprising:
a catheter configured to be introduced into a subject;
a robot configured to move the catheter within the subject in a robot reference frame, the robot being configured to provide a robot reference frame movement parameter indicative of a sequence of positions assumed by the catheter during movement of the catheter within the subject in the robot reference frame and to provide a series of robot time stamps corresponding to the sequence of positions assumed by the catheter;
a radiographic tracking imager configured to generate a series of radiographic tracking images in an image reference frame which radiographic tracking images show the catheter within the subject and to generate tracking time stamps representing acquisition times of each of the tracking radiographic images; and
a controller configured i) to convert the robot reference frame movement parameter from the robot reference frame to the image reference frame and ii) to synchronize the tracking time stamps and the robot time stamps wherein the controller is configure to stop generating the tracking images based on the sequence of positions and during the generating of the tracking images, to adjust by increasing and decreasing a frame rate of the tracking images based on the sequence of positions; further including a display and wherein the controller is further configured to control the display to display an overview image including roadmap information showing vessels along which the catheter can be moved, and when the tracking imager is stopped, draw a representation of a tip of the catheter on the overview image indicative of the sequence of positions based on the robot frame of reference movement parameter, and when the tracking imager is generating tracking images, overlying the tracking images on the overview image.

12. The interventional system as defined in claim 11, wherein the controller is configured to increase the frame rate in response to the robot reference frame movement parameter indicating the catheter is moving with a lower velocity and decrease the frame rate in response to the robot reference frame movement parameter indicating that the catheter is moving at a higher velocity.

13. The interventional system as defined in claim 11, wherein the controller is configured to set the frame rate in dependence on a direction of movement of the catheter.

* * * * *